United States Patent [19]
Dosch et al.

[11] Patent Number: 4,897,128
[45] Date of Patent: Jan. 30, 1990

[54] PROCESS OF DETERMINING THE ZINC CONTENT OF PHOSPHATING BATHS

[75] Inventors: Heinz Dosch; Dieter Hauffe, both of Frankfurt; Horst Gehmecker, Oberwiesen, all of Fed. Rep. of Germany

[73] Assignee: Metallgesellschaft Aktiengesellschaft, Frankfurt am Main, Fed. Rep. of Germany

[21] Appl. No.: 178,183

[22] Filed: Apr. 6, 1988

[30] Foreign Application Priority Data

Apr. 9, 1987 [DE] Fed. Rep. of Germany ....... 3711931

[51] Int. Cl.$^4$ ............................................. C23F 7/08
[52] U.S. Cl. ..................... 148/241; 148/262; 204/1 T; 204/405; 436/81
[58] Field of Search .................. 436/81; 148/241, 262; 204/1 M, 405

[56] References Cited

U.S. PATENT DOCUMENTS 3,479,152 11/1969 Overbeck et al. ................... 436/81
4,597,806 7/1986 Hauffe ............................. 148/241 X

OTHER PUBLICATIONS

"On-line-Titratoren för die Prozessanalytik vor Ort", Dipl.-Ing. F. Müller, Chemie-Technik, 15, Jahrgang (1986) Nr. 9, pp. 139–141.
Phosphating and Metal Pre-treatment, D. B. Freeman, Woodhead–Faulkner Cambridge in association with Pyrene Chemical Services Ltd., pp. 143 & 144, (1986).

*Primary Examiner*—G. L. Kaplan
*Attorney, Agent, or Firm*—Felfe & Lynch

[57] ABSTRACT

Described is a process for determining the zinc content of an acid aqueous phosphating bath. A bath sample is titrated at a pH value between 1.2 and 1.7 in the presence of ethylenediaminetetraacetic acid, hexamethylenetetramine and alkalihexacyanoferrate (III) with an alkalihexacyanoferrate(II) until the potential at an oxidation-reduction electrode immersed into the bath sample reaches an inflection point.

Any content of nitrite and/or iron(II) ions must be removed by an addition of nitrite-destroying substances and by an oxidation to iron(III) ions at a pH value above 8.

The process is particularly suitable for determining the zinc concentration of phosphating baths which contain 0.4 to 2.0 g/l Zn. The presence in phosphating baths of additional cations such as manganese and/or calcium and/or nickel and/or magnesium does not interfere with the process. The analysis can be automatic and may directly be used to control a metering device for supplying make-up concentrates to the phosphating bath.

8 Claims, No Drawings

PROCESS OF DETERMINING THE ZINC CONTENT OF PHOSPHATING BATHS

DESCRIPTION

The present invention is in a process for determining the zinc content of an acid aqueous phosphating bath and the use of that process to determine the zinc concentration of a phosphating bath which contains 0.4 to 2.0 g/l zinc. Preferably such baths contain additional components such as manganese, calcium, nickel and magnesium alone or in combination. The invention is also in a method to control metering apparatus for supplying make-up concentrates to the phosphating bath.

The analytic determination of the zinc content in the use of acid aqueous zinc phosphate solutions for a chemical surface treatment of steel and other metals is of great significance because in numerous modern processes, and particularly those used in low-zinc technology, it is essential to maintain the concentration of that bath component within narrow limits to obtain a high-quality phosphate layer.

It has become common practice to employ other cations, such as nickel, manganese, calcium and magnesium, in the phosphating bath to optimize the phosphate layers. Moreover, the increasing automation of the phosphating process requires the determination of the contents of the important bath components, particularly that of zinc, to be detected by automatic titrating devices in which the end point is preferably determined by electrochemical methods depending, e.g., on peaks and inflection points of the potential at indicator electrodes.

Presently, there is not a suitable method of determining the zinc content under the stated conditions. No. EP-A-171,842 describes a process of titrating zinc. However, the presence of manganese and calcium in the phosphating bath affects the titration by that process to such a degree that it cannot be used in practice unless cations, such as manganese and calcium, are substantially absent.

Therefore, it is an object of the present invention to provide a process for the determination of the zinc content of an acid aqueous phosphating bath which will not be affected particularly by the presence of manganese, nickel, calcium and magnesium and which permits an electrochemical indication of the end point of the titration.

THE INVENTION

To obtain the above-stated object and others, the process of the kind described first hereinbefore is carried out in accordance with the invention in such a manner that a bath sample is titrated at a pH value between 1.2 and 1.7 in the presence of ethylenediaminetetraacetic acid, hexamethylenetetramine and alkalihexacyanoferrate(III) with an alkalihexacyanoferrate(II) until the potential at an oxidation-reduction electrode immersed into the bath sample reaches an inflection point.

The consumption of alkalihexacyanoferrate(II) is a direct measure of the zinc content of the bath sample. 8.45 mg/l potassiumhexacyanoferrate(II) (calculated as $K_4[Fe(CN)_6] \cdot 3 H_2O$) correspond to 1.96 mg/l zinc.

It is important in the process of the invention that the pH value of the sample to be titrated is maintained in the relatively narrow range. A departure from that range will usually result in substantial errors in the concentration measurement. The combination of ethylenediaminetetraacetic acid and hexamethylenetetramine is also essential for the elimination of the otherwise disturbing influence of manganese, nickel, calcium and magnesium ions.

Ethylenediaminetetraacetic acid is preferably used as a solution of its alkali salt. 0.15 to 0.30 grams of that reagent are added to a 10-ml bath sample, which contains, e.g., 3 to 12 mg Mn, 4 to 15 mg Zn, 2 to 10 mg Ni and 1 to 2 mg Ca and which is diluted with about 70 ml deionized water. Hexamethylenetetramine is added to the bath sample in an amount of, e.g., 0.2 to 0.4 gram. Alkalihexacyanoferrate(III) in an amount of, e.g., 1 to 2 mg, is also added to the bath sample before the titration. Alkalihexacyanoferrate(III) is used to stabilize the potential.

The pH value of the sample to be titrated is preferably adjusted by the addition of a buffer consisting of phosphoric acid and monoalkaliphosphate in an amount of, e.g., 2 to 4 grams, calculated as $P_2O_5$, to a 10-ml bath sample. The titration is effected with alkalihexacyanoferrate(II) in the form of a normal solution (standard), which preferably contains also a certain quantity of alkalihexacyanoferrate(III).

In a preferred embodiment of the invention the bath sample is titrated against a platinum electrode, which usually consists of a saturated calomel single-rod measuring chain. The potential change from the beginning of the titration to the end point is about 350 mV.

If the bath sample contains nitrite, nitritedestroying substances, such as amidosulfonic acid in a quantity of, e.g., 0.05 to 0.25 g per 10 ml bath sample are added to the bath prior to titration.

Prior to the titration, any divalent iron contained in the bath sample should be removed by oxidation, i.e., precipitation. This can be accomplished by adjusting the pH value above 8 and maintaining the pH level for about 0.5 to 3 minutes. This condition will result in a fast oxidation of Fe(II) to Fe(III), e.g., by atmospheric oxygen and/or by oxidizers, such as chlorates, which are contained in or added to the bath sample. That step is necessary because the determination of the zinc content by the process of the invention is affected by the presence of divalent iron.

The process of the invention may be applied to special advantage to phosphating baths which contain 0.4 to 2 g/l zinc. Since the presence of manganese and/or calcium and/or nickel and/or magnesium in the bath sample will not disturb the process, it is particularly suitable for use with phosphating baths which contain such components.

A great advantage of the process of the invention is that the analytic determination is performed automatically and the detected difference between desired and actual values can be used in accordance with the invention to control a metering device to supply make-up concentrate to the phosphating bath, as described e.g., by F. Müller "On-line-Titratoren für die Prozessanalytik vor Ort" (Chemie-Technik, 15 (1986) No. 9, page 139 to 141).

It will be understood that the specification and examples are illustrative but not limitative of the present invention and that other embodiments within the spirit and scope of the invention will suggest themselves to those skilled in the art.

What is claimed is:

1. A method of determining the zinc content of an acid aqueous phosphating bath comprising:

providing a bath sample with a pH value between 1.2 and 1.7 with an oxidation-reduction electrode immersed therein; and titrating the bath sample in the presence of ethylenediaminetetraacetic acid, hexamethylenetetramine and alkalihexacyanoferrate(III) with an alkalihexacyanoferrate-(II) until the potential at the electrode reaches an inflection point.

2. The method of claim 1 wherein the bath sample is titrated against a platinum electrode.

3. The method of claim 1 wherein the bath sample contains nitrite and a nitrite-destroying substance is added prior to the titration.

4. The method of claim 3 wherein the nitritedestroying substance is amidosulfonic acid.

5. The method of claim 1 wherein the sample contains iron(II) ions, the pH of the sample is adjusted above 8 and the iron(II) ions are oxidized to iron(III)-ions before the bath sample is titrated.

6. The method of claim 1 wherein the zinc concentrations of the phosphating bath is 0.4 to 2.0 g/l Zn.

7. The method of claim 1 wherein the phosphating bath also contains cations of manganese and/or calcium and/or nickel and/or magnesium.

8. A method of controlling the zinc content of an acid aqueous zinc phosphating bath comprising:

determining the zinc content of the bath by providing a bath sample with a pH value between 1.2 and 1.7 with an oxidation-reduction electrode immersed therein;

titrating the bath sample in the presence of ethylenediameinetetraacetic acid, hexamethylenetetramine and alkalihexacyanoferrate(III) with an alkalihexacyanoferrate(II) until the potential at the electrode reaches an inflection point;

determining the consumption of alkalihexacyanoferrate(II) based on the electrode voltage potential; and supplying make-up concentrate by means of a metering device, which is controlled based on the consumption of alkalihexacyanoferrate(II).

* * * * *